(12) United States Patent
Arcot-Krishnamurthy et al.

(10) Patent No.: US 9,101,770 B2
(45) Date of Patent: Aug. 11, 2015

(54) HYPERTENSION THERAPY DEVICE WITH LONGEVITY MANAGEMENT

(71) Applicant: Cardiac Pacemakers, Inc., St. Paul, MN (US)

(72) Inventors: Shantha Arcot-Krishnamurthy, Vadnais Heights, MN (US); Eric A. Mokelke, White Bear Lake, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/185,737

(22) Filed: Feb. 20, 2014

(65) Prior Publication Data

US 2014/0257425 A1 Sep. 11, 2014

Related U.S. Application Data

(60) Provisional application No. 61/774,092, filed on Mar. 7, 2013.

(51) Int. Cl.
*A61N 1/00* (2006.01)
*A61N 1/36* (2006.01)
*A61N 1/372* (2006.01)

(52) U.S. Cl.
CPC ........ *A61N 1/36117* (2013.01); *A61N 1/36139* (2013.01); *A61N 1/36167* (2013.01); *A61N 1/36175* (2013.01); *A61N 1/36178* (2013.01); *A61N 1/37235* (2013.01)

(58) Field of Classification Search
CPC .................................................... A61N 1/36
USPC ............................................................ 607/44
See application file for complete search history.

(56) References Cited

U.S. PATENT DOCUMENTS

| 7,373,204 B2 | 5/2008 | Gelfand et al. |
| 8,150,521 B2 | 4/2012 | Crowley et al. |
| 8,195,290 B2 | 6/2012 | Brockway et al. |
| 2006/0064139 A1* | 3/2006 | Chung et al. .................... 607/45 |

* cited by examiner

*Primary Examiner* — Robert N Wieland
(74) *Attorney, Agent, or Firm* — Schwegman Lundberg & Woessner, P.A.

(57) ABSTRACT

System and methods for programming and delivering electrical stimulation to treat hypertension are discussed. In various embodiments, an ambulatory stimulator system, such as an implantable medical device, can receive a power-saving command and deliver the electrical stimulation to a target site in a patient according to one or more simulation parameters including a therapy on-off pattern. In some embodiments, stimulation with therapy on-off pattern can reduce the power consumption while maintaining the anti-hypertension therapy efficacy. In some embodiments, the ambulatory stimulator system can include one or more of a physiologic response detector, a patient status detector, or a battery longevity detector. The power-saving command can be generated using one or more of the detected physiologic signal, the patient status, or the information about the battery longevity.

20 Claims, 8 Drawing Sheets

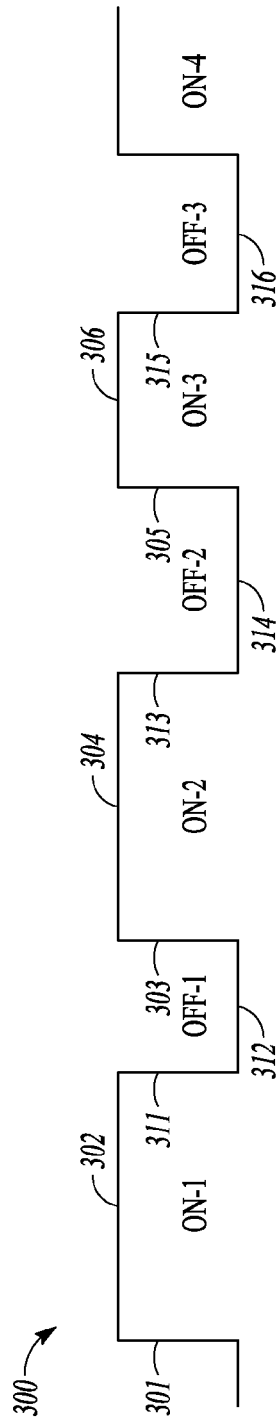
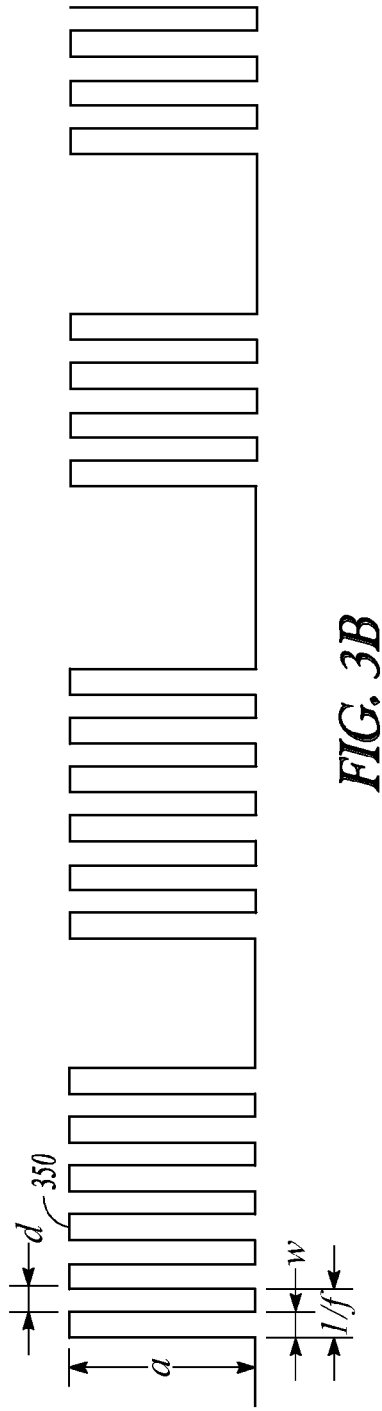
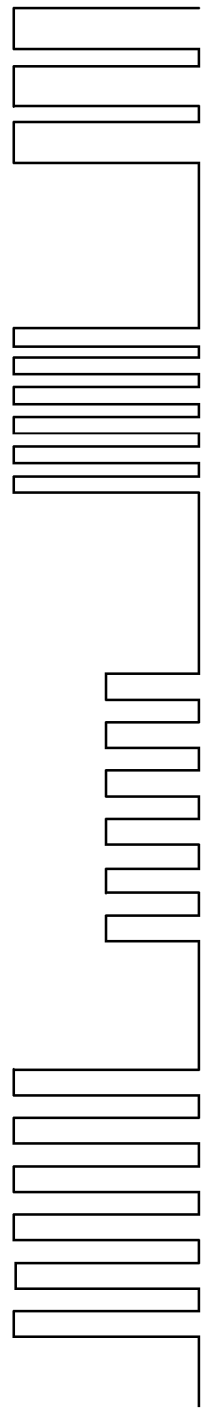
FIG. 3A
FIG. 3B
FIG. 3C

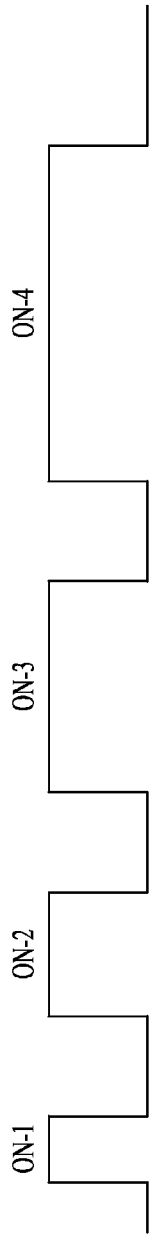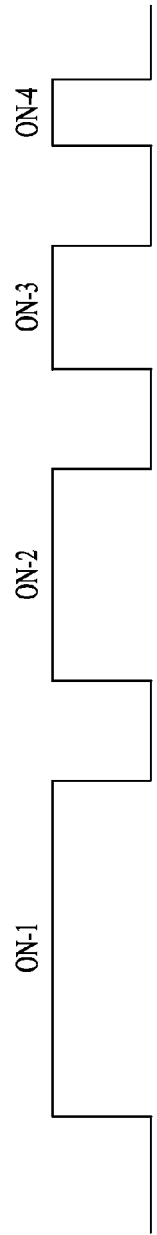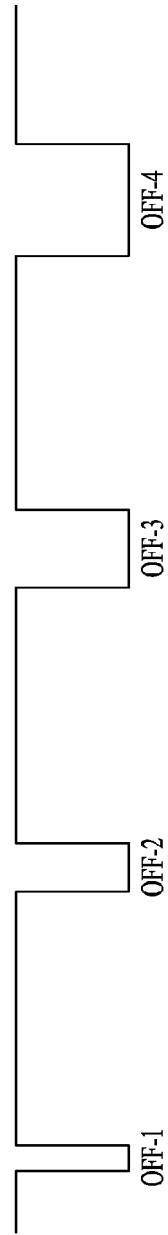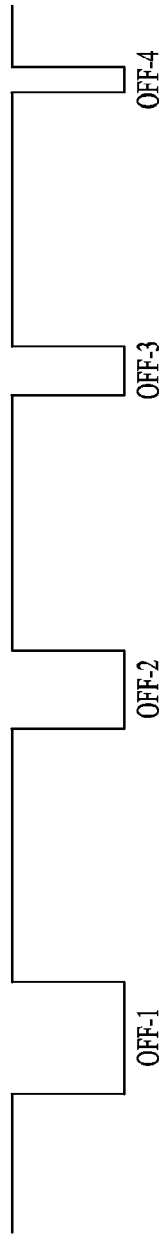
FIG. 5A
FIG. 5B
FIG. 5C
FIG. 5D

HYPERTENSION THERAPY DEVICE WITH LONGEVITY MANAGEMENT

CLAIM OF PRIORITY

This application claims the benefit of priority under 35 U.S.C. §119(e) of U.S. Provisional Patent Application Ser. No. 61/774,092, filed on Mar. 7, 2013, which is herein incorporated by reference in its entirety.

TECHNICAL FIELD

This document relates generally to medical devices, and more particularly, to systems, devices and methods for treating hypertension with device longevity management.

BACKGROUND

Hypertension, or high blood pressure, refers to a transitory or sustained elevation of systemic arterial blood pressure to a level that is likely to induce cardiovascular damage or other adverse consequences. Hypertension has been arbitrarily defined as a systolic blood pressure above 140 mmHg or a diastolic blood pressure above 90 mmHg. For patients suffering from hypertension, the long term mortality as well as the quality of life can be improved if blood pressure can be reduced. However, many hypertension patients may not respond to treatments related to lifestyle changes or anti-hypertension drugs. Consequences of uncontrolled hypertension include, but are not limited to, retinal vascular disease and stroke, left ventricular hypertrophy, heart failure, myocardial infarction, dissecting aneurysm, and endovascular disease. Therefore, there is a need for controlling blood pressure in these patients.

SUMMARY

Electrical stimulation system can be used to treat hypertension. Examples of such electrical stimulation system can include an implantable anti-hypertension (AHT) stimulator. The AHT stimulator can be configured to stimulate a pressoreceptor region such as a baroreceptor. Baroreceptors include afferent nerves and sensory nerve endings that are sensitive to the stretching of the wall that results from increased blood pressure from within, and function as the receptor of a central reflex mechanism that tends to reduce the pressure. Activation of baroreceptors can cause baroreflex inhibition of sympathetic nerve activity and a reduction in systemic arterial pressure by decreasing peripheral vascular resistance.

An implantable AHT stimulator can include a power source (such as a battery) used for generating AHT stimulation pulses. The longevity of the battery depends at least in part on the stimulation parameters selected for chronic AHT stimulation. For example, stimulation with higher pulse amplitude and longer pulse width consumes more power. Because some implantable AHT stimulators are powered by non-rechargeable batteries, a device replacement may be necessary when the battery is depleted. The device replacement generally requires surgery which poses risks to patient and incurs additional cost. It is therefore desirable that the AHT stimulator have prolonged battery life while maintaining the AHT therapy efficacy.

Various embodiments discussed herein improve the battery life of an ambulatory stimulator system while maintaining the efficacy of the stimulation therapy. For example, a system for treating hypertension, such as an implantable AHT device, can include a stimulator configured to generate stimulation pulses. The device can have a memory configured to store one or more stimulation parameters including a therapy-on period during which the stimulation pulses are programmed to be delivered, a therapy-off period during which no stimulation pulse is programmed to be delivered, and a therapy on-off pattern including a combination of a sequence of therapy-on periods with variable durations and a sequence of therapy-off periods with variable durations. The therapy on-off patterns can be used to conserve the power consumption for AHT therapy. A control circuit can be configured to receive a power-saving command, time one or both of the therapy-on period and the therapy-off period, and schedule the delivery of the stimulation pulses to a target site according to the therapy on-off pattern in response to a power-saving command.

A method for treating hypertension can include receiving a power-saving command, programming one or more stimulation parameters in response to the power-saving command, generating the stimulation pulses in accordance with the programmed stimulation parameters, and delivering to the stimulation pulses to a target site such as a baroreceptor region or a neural target. The one or more stimulation parameters can include a therapy-on period during which stimulation pulses are programmed to be delivered, a therapy-off period during which no stimulation pulse is programmed to be delivered, and a therapy on-off pattern defining a combination of a sequence of therapy-on periods with variable durations and a sequence of therapy-off periods with variable durations. Programming the parameters such as the therapy on-off pattern can conserve the power consumption for AHT therapy while maintaining the AHT therapy efficacy.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 3A-C illustrate, by way of example, embodiments of the stimulation pulse train generated according to a therapy on-off pattern.

FIGS. 5A-D illustrate, by way of example, embodiments of therapy on-off pattern with gradual changes in therapy-on or therapy-off durations.

DETAILED DESCRIPTION

The following detailed description of the present subject matter refers to the accompanying drawings which show, by way of illustration, specific aspects and embodiments in which the present subject matter may be practiced. These embodiments are discussed in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein are systems, devices and methods for stimulating various regions in the body in an effort to induce a desired response such as a manageable reduction in blood pressure, and at the same time conserving the energy consumption for stimulation without compromise to the efficacy of stimulation therapy. Various stimulation sites have been identified, such as nerve endings, nerve bundles, and baroreceptors. For example, some embodiments stimulate baroreceptor sites in the carotid sinus or pulmonary artery. Some embodiments involve stimulating either baroreceptor sites or nerve endings in the aorta, one or more chambers of the heart, fat pads of the heart, or an afferent nerve trunk such as the vagus, carotid and aortic nerves. Some embodiments stimulate afferent nerve trunks using a cuff electrode. Some embodiments stimulate afferent nerve trunks using an intravascular lead positioned in a blood vessel proximate to the nerve, such that the electrical stimulation passes through the vessel wall to stimulate the afferent nerve trunk. Various embodiments reduce the energy consumption by automatically putting the stimulation system or the stimulation device into a power-saving mode, and program one or more stimulation parameters including therapy on-off pattern using the information such as the device status and the patient response to the stimulation therapy.

Figure 1:
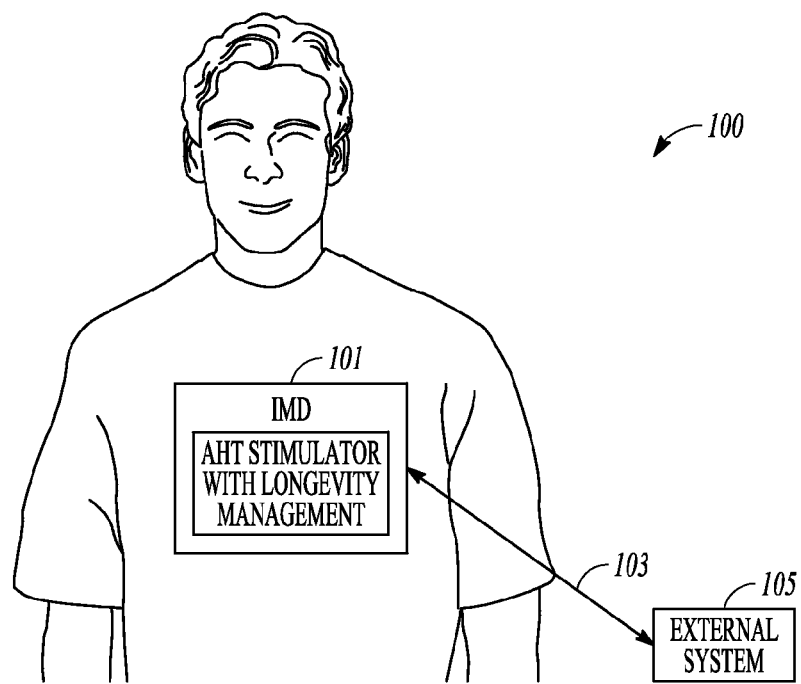
FIG. 1 illustrates, by way of example, an embodiment of an implantable stimulator system and portions of the environment in which the implantable stimulator system operates.

FIG. 1 illustrates, by way of example, an embodiment of an implantable stimulator system 100 and portions of the environment in which the implantable stimulator system 100 operates. The implantable stimulator system 100 includes an implantable medical device (IMD) 101 and an external system 105 that communicates with the IMD 101 via a communication link 103.

In some embodiments, the IMD 101 can be an implantable neural stimulator configured to generate and deliver stimulation pulses to a target site on or within the body. The implantable neural stimulator may be configured to provide anti-hypertension (AHT) therapy to treat hypertension. In various embodiments, the IMD 101 can include a neural stimulation (NS) subsystem and a cardiac rhythm management (CRM) subsystem. The NS subsystem and the CRM subsystem can be two separate devices, or two separate circuits within the IMD 101. The NS subsystem can include circuits and instructions to generate and deliver the stimulation pulses to one or more target neural stimulation sites. In some embodiments, as illustrated in FIG. 1, the NS subsystem includes an anti-hypertension (AHT) stimulator with longevity management function. The CRM subsystem can include circuits and instructions to generate and deliver the cardiac therapies to one or more target cardiac therapy sites. In some embodiments, the CRM subsystem can provide cardiac pacing, cardiac resynchronization, cardioversion, cardiac defibrillation, or other cardiac therapies. The IMD 101 can also include one or more monitoring or therapeutic devices, subcutaneously implanted device, a wearable external device, a drug delivery device, a biological therapy device, and other ambulatory medical devices.

Various embodiments of IMD 101 deliver therapy, such as electrical stimulation pulses, to the target sites via a therapy delivery system. The delivery system can include one or more leads coupled to the IMD 101. Each lead may include one or more electrodes along the lead body. In some embodiments, the lead may be external to the patient, and the electrodes on the leads can be placed in and affixed to a target stimulation site on the patient's skin. In some embodiments, the lead can be subcutaneously or transvenously placed inside the patient, and the electrodes can be placed to a target stimulation side internal to the patient. The leads can be temporarily placed or chronically implanted. In some embodiments, the therapy delivery system may include wireless stimulation using acoustic, radio-frequency, microwave, or other forms of energy other than electricity pulses.

The target stimulation site can be a baroreceptor region such as an aortic arch, carotid sinuses of the left and right internal carotid arteries, a carotid body, cardiac fat pads, and vena cava. Additionally, a baroreceptor region may include afferent nerve trunks, such as the vagus, aortic and carotid nerves, leading from the sensory nerve endings. Stimulating baroreceptors inhibits sympathetic nerve activity and reduces systemic arterial pressure by decreasing peripheral vascular resistance and cardiac contractility.

In various embodiments, the implantable stimulator system 100 can sense a physiological signal from the patient. The IMD 101, either alone or in combination with the external system 105, can be configured to monitor and assess the effectiveness of stimulation pulses in capturing the tissue at the target stimulation site while causing no trauma to the tissue. The physiologic signal can be obtained from an external physiologic sensor, an internal physiologic sensor, or a physiologic sensor contained within the IMD 101. The physiologic signal can be coupled to the IMD 101 or transmitted to the external system 105. In some embodiments, the electrodes used for stimulating the target site can also be configured to sense the physiologic signal. Examples of the physiological signals include electrocardiogram, electrograms, arterial pressure, pulmonary artery pressure, RV pressure, LV coronary pressure, coronary blood temperature, blood oxygen saturation, heart sounds, respiration signals, and nerve activity. The IMD 101 can include circuits to analyze the sensed physiologic signals and adjust the stimulation pulses or re-schedule the delivery the stimulation pulses through a feedback-control system.

The external system 105 can be configured to allow for programming the IMD 101 and receiving the signals acquired by the IMD 101 via a communication link 103. In one embodiment, the external system 105 can be a programmer. In another embodiment, the external system 105 can be a remote patient management system that monitors patient status or adjusts therapies from a remote location. The programmer 105 can include a user-interface configured to present to the system operator (such as a clinician) the information about patient status and system status. Alternatively or additionally, the programmer 105 can include a user-input device configured to enable the system operator to program the IMD 101 such as adjusting the parameters of the AHT therapy.

The communication link 103 can provide for data transmission between the IMD 101 and the external system 105. Examples of the communication link 103 include an inductive telemetry link, a radio-frequency telemetry link, or a telecommunication link such as an internet connection. The data transmitted through the communication link 103 can include, for example, physiological data acquired by IMD 101, therapy history data, data representing the operational status of the IMD 101, battery status, instructions to the IMD 101 such as data acquisition, sensor and sensing electrodes configuration, device self-diagnostic test, or delivery of therapy.

In various embodiments, the IMD 101 and the external system 105, including their various elements discussed in this document, are implemented using a combination of hardware and software. In various embodiments, each element of IMD 101 and external system 105 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" can include, among other things, an electronic circuit comparator constructed to perform the only function of a comparison between two signals or a portion of a general-purpose circuit driven by a code instructing that portion of the general-purpose circuit to perform the comparison between the two signals.

Figure 2:
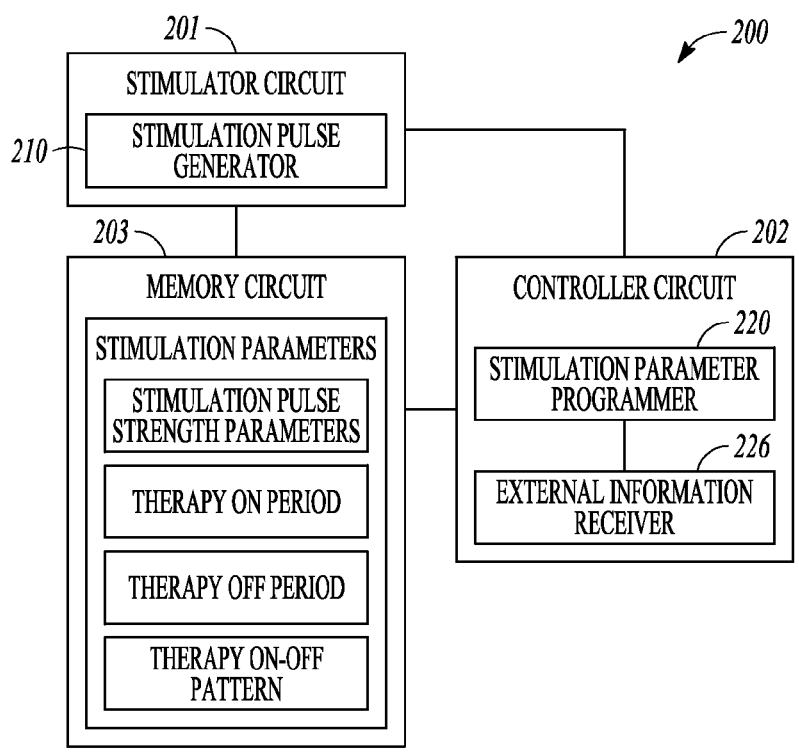
FIG. 2 illustrates, by way of example, an embodiment of an anti-hypertension (AHT) stimulator system.

FIG. 2 illustrates, by way of example, an embodiment of an AHT stimulator system 200 for treating hypertension. The AHT stimulator system 200 includes a stimulator circuit 201, a controller circuit 202, and a memory circuit 203. System 200 represents an embodiment of the IMD 101, or the neural stimulation subsystem of the IMD 101.

The stimulator circuit 201 includes a stimulation pulse generator 210 configured to generate electrical stimulation pulses. The controller circuit 202 is connected to the stimulator circuit 201 and the memory circuit 203. In various embodiments, the controller circuit 202 can be configured to control the generation and delivery of the stimulation pulses such as for stimulating a target for AHT therapy. According to various embodiments, the controller circuit 202 may include a stimulation parameter programmer 220 and an external information receiver 226. The stimulation parameter programmer 220 can be configured to adjust one or more programmable stimulation parameters stored in the memory circuit 203 when certain condition is met. As illustrated in FIG. 2, examples of the programmable stimulation parameters stored in the memory circuit 203 may include stimulation pulse strength parameters, therapy-on period, therapy-off period, and therapy on-off pattern. The stimulation pulse strength parameters include parameters that define the morphology of the pulse and of the pulse train, such as stimulation pulse strength parameters include a pulse amplitude, pulse width, pulse morphology, inter-pulse interval, pulse duty cycle, and pulse frequency. The pulse morphology may include one of a square wave, triangle wave, sinusoidal wave, or other waves with desired harmonic components to mimic white noise such as is indicative of naturally-occurring baroreflex stimulation. The stimulation pulse strength parameters control the amount of energy delivered to the target site within a unit time. In various embodiments, the energy consumed by the stimulator is proportional to the stimulation pulse strength parameters. For example, a higher amplitude, a wider pulse-width, and higher pulse frequency correspond more energy delivered to the target site.

The programmable stimulation parameters may also include therapy schedule parameters that control the time and duration of the stimulation pulse train, such as the therapy-on period during which the stimulation pulses are programmed to be delivered, the therapy-off period during which no stimulation pulse is programmed to be delivered, and the therapy on-off pattern which determines the timing of the initiation of the therapy-on period and the initiation of the therapy-off period. In some embodiments, the therapy on-off pattern defines a combination of a sequence of therapy-on periods with variable durations and a sequence of therapy-off periods with variable durations. Examples of the therapy on-off pattern are discussed below, such as with reference to FIGS. 3-5.

In various embodiments, the stimulation parameter programmer 220 can be configured to adjust the programmable stimulation parameters in response to a power-saving command. The power-saving command may be generated automatically using the external information provided through the external information receiver 226. For example, the controller circuit 202 may receive from the external information receiver 226 one or more of a patient's physiologic information, system status information, and other environmental or contextual information. If the received external information indicates a change of patient status or a change of system status that meets a specified criterion, the controller circuit 202 may generate or receive from the system operator a power-saving command. Upon receiving the power-saving command, the stimulation parameter programmer 220 can retrieve from the memory circuit 203 one or more stored stimulation parameters and adjust the one or more stimulation parameters using the patient's physiologic information or system status information. Examples of the automatic stimulation parameter adjustment using patient or system status information are discussed below, such as with reference to FIGS. 6-7.

In some embodiments, the external information receiver 226 may include a circuit configured to communicate with the programmer or another external or internal device via a wired or wireless communication link, such as an inductive telemetry or radio-frequency telemetry. From the programmer or the external or internal device, the controller circuit 202 may receive the system operator's programming input through the external information receiver 226. In some embodiments, the programmer or the external device can include a user-interface enabled to present to the system operator the information about the patient status and the system status. In some embodiments, the user interface includes a user input device allowing the system operator to program or adjust the one or more stimulation parameters. In various embodiments, the programming or adjustment of the stimulation parameters can be enabled in response to a power-saving command provided manually by the system operator through the user-interface.

In some embodiments, the stimulation parameter programmer 220 can chronically adjust the one or more stimulation parameters when the external information receiver 226 receives the information such as patient's newly developed or worsened disease, medical procedure performed, or environmental change. In some embodiments, the stimulation parameter programmer 220 can adjust the one or more stimulation parameters regularly or periodically. In some embodiments, the stimulation parameter programmer 220 can select from a number of values for a stimulation parameter pre-stored in the memory circuit 203. For example, when a patient switches from an awake state to a sleep state, the stimulation parameter programmer 220 can select a different therapy on-off pattern from a number of pre-stored therapy on-off patterns in the memory circuit 203. In some embodiments, the stimulation parameter programmer 220 adjusts or reprograms the one or more stimulation parameters temporarily. For example, when a clinician performs a device test in clinic (for example, to optimize the therapy programming), the stimulation parameters may be temporarily switched from the present setting to a temporary test mode. Upon the completion of the test, the stimulation parameters may be reprogrammed back to the original setting, or to a newly prescribed setting.

FIGS. 3A-C illustrate, by way of example, embodiments of the stimulation pulse train generated according to a therapy on-off pattern 300. The therapy on-off pattern 300 defines a combination of a sequence of therapy-on periods with variable durations (e.g., ON-1, ON-2, and ON-3) and a sequence of therapy-off periods with variable durations (e.g., OFF-1, OFF-2, and OFF-3). Within the therapy on-off pattern 300, the durations of the therapy-on periods (e.g., 302 for ON-1, 304 for ON-2, and 306 for ON-3) may be identical or different, and the durations of the therapy-off periods (e.g., 312 for OFF-1, 314 for OFF-2, and 316 for OFF-3) may be identical or different. As illustrated in FIG. 3A, the therapy on-off pattern 300 include the onset timing of the therapy-on periods 301, 303 and 305; and the onset timing of the therapy-off periods 311, 313 and 315. In some embodiments, the therapy on-off pattern 300 can be characterized by a sequence of therapy-on periods with gradually shortened durations. In other embodiments, the therapy on-off pattern can be characterized by a sequence of therapy-off periods with gradually prolonged durations. A sequence of variable therapy-off periods during the stimulation may be beneficial to reduce the power consumption by the stimulator without compromising the desired efficacy of the AHT therapy.

FIG. 3B illustrates, by way of example, a simulation pulse train comprising a plurality of pulses 350 during the therapy-on periods. The therapy-on periods and the therapy-off periods are defined by the therapy on-off pattern 300 as shown in FIG. 3A. The stimulation pulses 350 can be characterized by stimulation strength parameters such as stimulation amplitude a, pulse width w, inter-pulse interval d, stimulation frequency f, pulse cycle length 1/f which is equal to the sum of w and d, pulse duty cycle which is equal to the product of w and f, and other parameters equivalent to or derivable from the parameters as illustrated in FIG. 3B. The stimulation pulses 350 can also be characterized by pulse morphology, which in this example is uniphasic square wave. Other embodiments of the pulse morphology may include triangle wave, sawtooth wave, truncated wave, and random wave. The waveform may be in the form of multiphasic waves including biphasic, triphasic, or multiphasic waves. As illustrated in FIG. 3B, the stimulation strength and pulse morphology are uniform across all pulses during all therapy-on periods.

The stimulation strength parameters and pulse morphology can be different among the sequence of therapy-on periods. As illustrated in FIG. 3C, pulse amplitude during the therapy-on period ON-2 is reduced from an earlier value during the therapy-on period ON-1; pulse frequency is increased during the therapy-on period ON-3; and pulse width (and pulse duty cycle) is increased during the therapy-on period ON-4. Varying the stimulation strength parameters can result in different amount of energy delivered to the target site. Similar to the variable therapy-off periods that may reduce the stimulator's energy consumption while maintaining the stimulation therapy efficacy, introducing variable stimulation strength parameters may also reduce the energy requirement for an AHT therapy.

Figure 4A:
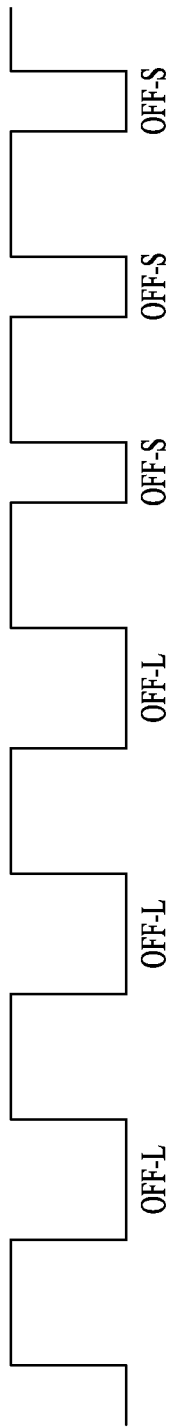
FIGS. 4A-C illustrate, by way of example, embodiments of a therapy on-off pattern with variable therapy-off periods.
Figure 4B:
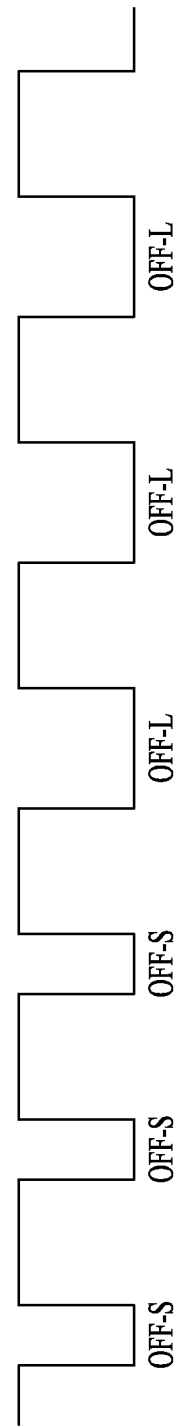
Figure 4C:
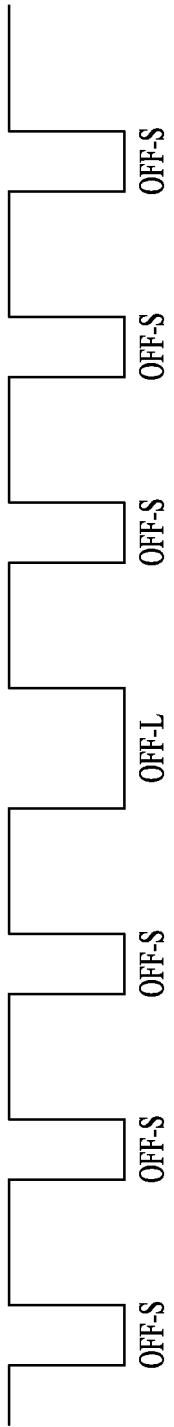

FIGS. 4A-C illustrate, by way of example, embodiments of a therapy on-off pattern with variable therapy-off periods. The therapy on-off pattern can include a combination of a sequence of therapy-on periods with a constant duration and a sequence of therapy-off periods with two distinct therapy-off durations: a longer duration OFF-L and a shorter duration OFF-S. Various therapy on-off patterns, as illustrated in FIGS. 4A-C, can be formed by arranging the order of the therapy-off periods with duration OFF-L and the therapy-off periods with duration OFF-S. The variable therapy-off duration can reduce the power consumption while maintaining the efficacy of the AHT therapy.

FIG. 4A illustrates, by way of example, a therapy on-off pattern with a sequence of therapy-off periods with longer duration OFF-L followed by a sequence of therapy-off periods with shorter duration OFF-S. This therapy on-off pattern may be desirable when stimulation with a longer therapy-off duration OFF-L is less effective in achieving the blood pressure reduction; thus a shorter therapy-off duration OFF-S can be attempted to increase the amount of energy delivered to the target site in a unit time to achieve the desired level of reduction in blood pressure. This therapy on-off pattern may also be used as a transition from a power-saving mode (which, for example, can be characterized by longer duration or more frequent therapy-off periods) to an ambulatory therapy mode (which, for example, can be characterized by shorter duration of or less frequent therapy-off periods).

FIG. 4B illustrates, by way of example, a therapy on-off pattern with a sequence of therapy-off periods with shorter duration OFF-S followed by a sequence of therapy-off periods with longer duration OFF-L. This therapy on-off pattern may be desirable when stimulation with a shorter therapy-off duration OFF-S has effectively and satisfactorily reduced the blood pressure; thus a longer therapy-off duration OFF-L can be attempted to decrease the amount of energy consumption without significantly reducing the therapy efficacy. This therapy on-off pattern may also be used as a transition from an ambulatory therapy mode to a power-saving mode, such as upon the receipt of a power-saving command from the system operator or generated automatically according to patient's physiological signals indicating a well-managed blood pressure.

FIG. 4C illustrates, by way of example, a therapy on-off pattern with an intermittent long-duration (OFF-L) therapy-off period within a sequence of therapy-off periods with shorter duration OFF-S. That is, the therapy-off periods with duration OFF-L are infrequently introduced. Introducing frequent therapy-off periods with shorter duration OFF-S is desirable in reducing the total energy consumption while maintaining the therapy efficacy. In one example, the OFF-L duration can be in the range of approximately 1-2 minutes, and the OFF-S duration can be in the range of approximately 1-30 seconds. In some embodiments, the OFF-S duration can be selected to be short enough such that it cannot cause substantial fluctuation in blood pressure during the transitions between the therapy-on and therapy-off periods, while at the same time achieve desirable energy reduction. In some other embodiments, the therapy-off period with duration OFF-L may be eliminated and replaced with a sequence of therapy-off periods with the shorter duration OFF-S, such that the therapy remains effective in maintaining the desirable controlled blood pressure while the total energy consumption is reduced.

FIGS. 5A-D illustrate, by way of example, embodiments of therapy on-off pattern with gradual changes in therapy-on or therapy-off durations. Such therapy on-off patterns may be used in a process of finding a desirable therapy-on period or a therapy-off period that provides satisfactory therapy efficacy with the reduced energy delivered to the target site. These patterns may also be used during transitions from an ambulatory therapy mode to a power-saving mode (e.g., FIGS. 5B and 5C), or from a power-saving mode to an ambulatory therapy mode (e.g., FIGS. 5A and 5D).

FIG. 5A illustrates, by way of example, a therapy on-off pattern with gradual increase in the duration of the therapy-on periods. This therapy on-off pattern may be used in occasions where increased stimulation is desired to achieve improved therapy outcome (i.e., more substantial decrease in blood pressure). For example, the duration increases in a "step-up" fashion from ON-1 during the initial therapy-on period, to ON-2, ON-3 and ON-4 during subsequent therapy-on periods. In some embodiments, the therapy-on period may be initialized to a pre-determined first duration value $ON_{min}$. The therapy-on duration then increases by a step-size of increment δ in the subsequent therapy-on periods, until either a pre-determined second duration value $ON_{max}$ is reached or a desirable patient's physiological response to stimulation is achieved.

FIG. 5B illustrates, by way of example, a therapy on-off pattern with gradual decrease in the duration of the therapy-on periods. This therapy on-off pattern may be used during the process of searching for a shortest therapy-on duration that is adequate to maintain the efficacy of anti-hypertension therapy, while at the same time the energy consumption is substantially reduced. As illustrated in FIG. 5B, the duration decreases in a "step-down" fashion from ON-1 during the initial therapy-on period, to ON-2, ON-3 and ON-4 during subsequent therapy-on periods.

FIG. 5C illustrates, by way of example, a therapy on-off pattern with gradual increase in the duration of the therapy-off periods. The duration increases in a "step-up" fashion from OFF-1 during the initial therapy-off period, to OFF-2, OFF-3 and OFF-4 during subsequent therapy-off periods. This therapy on-off pattern may be used during the process of searching for a therapy-off duration that maintains the efficacy of AHT therapy without causing substantial fluctuation in blood pressure during the transitions between the therapy-on and therapy-off periods thereby, while at the same time reduce the total energy consumption.

FIG. 5D illustrates, by way of example, a therapy on-off pattern with a gradual decreases in the duration of the therapy-off periods. The duration decreases in a "step-down" fashion from OFF-1 during the initial therapy-off period, to OFF-2, OFF-3 and OFF-4 during subsequent therapy-off periods. This therapy on-off pattern may be used in occasions where increased stimulation is desired to achieve improved therapy outcome (i.e., more substantial decrease in blood pressure).

While FIGS. 5A-D illustrate embodiments of adjusting either only therapy-on period duration (FIGS. 5A and 5B) or only therapy-off period duration (FIGS. 5C and 5D) in a step-up or step-down fashion, some embodiments of the therapy on-off patterns may allow both the therapy-on periods and the therapy-off periods to gradually change in a step-up or step-down fashion. One example of the therapy on-off pattern can include a combination of therapy-on periods with "step-up" increase in duration and therapy-off periods with "step-down" decrease in duration. Because the "step-up" in therapy-on duration (FIG. 5A) has the similar effect as the "step-down" in therapy-off duration (FIG. 5D) of increasing the stimulation energy delivered to the target site, this therapy on-off pattern can expedite the transition from a power-saving mode to an ambulatory therapy mode. In another example, the therapy on-off pattern can include a combination of the therapy-on periods with "step-down" decrease in duration and therapy-off periods with "step-up" increase in duration. Because the "step-down" in therapy-on duration (FIG. 5B) has the similar effect as the "step-up" in therapy-off duration (FIG. 5C) of reducing the stimulation energy delivered to the target site, this therapy on-off pattern can expedite the transition from an ambulatory therapy mode to a power-saving mode.

Figure 6:
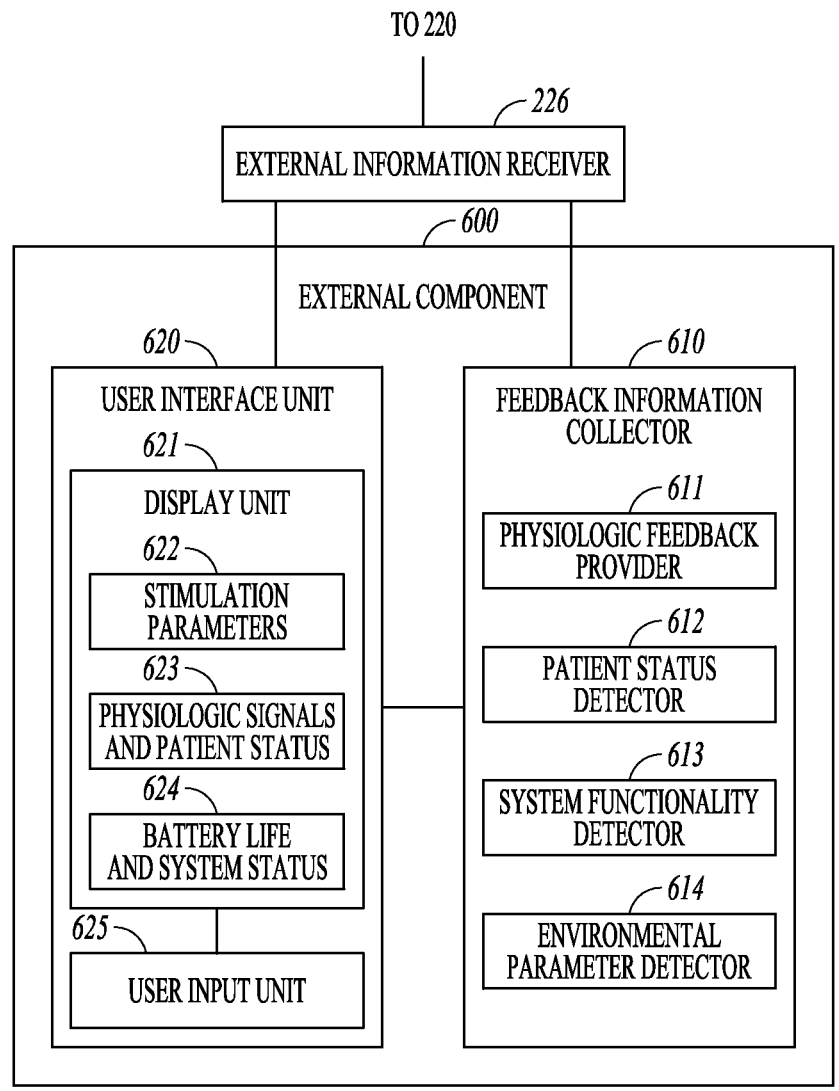
FIG. 6 illustrates, by way of example, an embodiment of external components of the stimulation system.

FIG. 6 illustrates, by way of example, an embodiment of external components 600 that can be used with the stimulation system 200. The external components 600 are configured to be coupled to the stimulation system 200 via the external information receiver 226. The external components 600 can provide feedback and user input to the stimulation system 200.

The external components can include a feedback information collector 610 and a user interface 620. In some embodiments, either one or both of the feedback information collector 610 and the user interface unit 620 can be made detachable from the rest of the system, where the external information receiver 226 can be configured to interface between the external components 600 and the rest of the stimulation system. In other embodiments, either one or both of the feedback information collector 610 and the user interface unit 620 may be integrated with the rest of the system. In an embodiment, the user interface unit 620 may be implemented in the external system 105 as shown in FIG. 1, and the feedback information collector 610 may be implemented in the IMD 101. In another embodiment, the feedback information collector 610 may be implemented distributedly between the IMD 101 and the external system 105.

The feedback information collector 610 can be configured to sense and acquire the information from the patient and the information from the system indicating the system operation status, and provide the information to the controller circuit 202 via the external information receiver 226. The feedback information collector 610 may be integrated within IMD 101, or it may be implemented in separate unit(s) outside the IMD 101 and communicating with the IMD 101. As illustrated, the feedback information collector 610 can include a physiologic feedback provider 611, a patient status detector 612, a system functionality detector 613, and an environmental parameter detector 614. The physiologic feedback provider 611 may be coupled to a physiologic sensor attached to or implanted in the patient. The physiologic sensor may be enabled to sense a physiologic signal from the patient during the therapy delivery. Examples of the sensors or sensor modalities include impedance, pressure, acceleration, temperature, and other sensors. Examples of the physiologic signal may include electrocardiogram, electrograms, arterial pressure, pulmonary artery pressure, RV pressure, LV coronary pressure, coronary blood temperature, blood oxygen saturation, heart sounds, respiration signals, nerve activity, nerve traffic, and other ANS activity.

The patient status detector 612 detects patient condition before, during, and after the stimulation therapy, such as AHT therapy, is delivered. In some embodiments, the patient status detector 612 detects patient comfortness, level of shortness of breath, dizziness, posture, awakeness or sleep state, alertness, and activity level. The patient status detector 612 may be configured to be connected to a sensor internal or external to the patients which detects the patient status. Examples of the sensors for detecting patient status can include an accelerometer that detects the posture or activity level of the patient, a transthoracic impedance sensor that detects the minute ventilation and thereby the activity level of the patient, a bioelectric sensor detects the brain activity and thereby the sleep state or awakeness of the patient. In some embodiments, the patient status detector 612 may be configured to receive system operator's input that contains assessment of patient status such as patient comfortness to a delivered therapy, patient's medication and treatment information, such as a recent surgery received.

The system functionality detector 613 is configured to detect the functionality and integrity of the stimulation system, including one or more of lead integrity, sensing configuration, stimulation protocol, battery status, and battery longevity. The functionality and integrity of the stimulation system may also include, for example, charge density, therapy delivery status such as cardiac pacing delivery, cardiac defibrillation delivery, neural stimulation delivery, and drug delivery. The environmental parameter detector 614 detects the environmental and contextual conditions involving ambient environment of the patient, such as air temperature, atmospheric pressure, and time of the day (day or night).

The user interface unit 620 includes a display unit 621 and a user input unit 625. The display unit 621 can be configured to generate patient and system information in a readable format and displays the information on a screen. As illustrated in FIG. 6, the user interface unit 620 is connected to the feedback information collector 610; the information acquired from the feedback information collector 610, including one or more of physiologic feedback information, patient status, system functionality information, and environmental and contextual information may therefore be made available to the user interface unit 620. In various embodiments, the display unit 740 may generate and display the information regarding stimulation parameters 622, physiologic signals and patient status information 623, and battery life and system status information 624. The stimulation parameter 622 may include present setting of the one or more stimulation parameters such as pulse amplitude, pulse width, pulse waveform, frequency, therapy-on period and therapy-off period, and therapy on-off pattern. Physiologic signals and patient status 623 may include physiologic sensor signals acquired during the therapy and signal statistics or signal metrics. Physiologic signals and patient status 623 may also include quantized categorical levels of patient status including patient activity levels or postures. Battery life and system status 624 may include the battery longevity indicator, along with the historical record of battery use and stimulation parameter settings.

The user input unit 625 may either be separated from the display unit 621, or be integrated with the display unit 621 where the display unit is equipped with user control capabilities, such as a touch-screen. The user input unit 625 can be configured to allow the user to manually adjust the one or more stimulation parameter with reference to the information presented from the display unit 621. In an embodiment, the user input unit allows the user to define a therapy on-off pattern with customized arrangement of a number of therapy-on periods with variable durations and a number of therapy-off periods with variable durations. In another embodiment, the user input unit allows the user to select from a plurality of therapy on-off patterns stored in the system and displayed in the display unit 621.

In some embodiments, the external information receiver 226 receives the feedback information from the feedback information collector 610, processes the feedback information (including, for example, patient's physiologic response to stimulation, patient status, and estimated battery longevity), and generates a recommendation for adjusting the one or more stimulation parameters, such as therapy on-off pattern. The recommendation may then be presented to the system operator from the display unit 621, where the system operator may make confirmation or manual adjustment of the recommended parameters using the user input unit 625. In an embodiment, the recommendation of the stimulation parameters can be performed automatically when the system operates in an ambulatory therapy mode, where the external information receiver 226 receives from the feedback information collector 610 and evaluates the feedback information continuously or periodically. In some examples, the external information receiver 226 can be configured to evaluate the feedback every 1-2 hours, daily, weekly, or any period prescribed and programmed by a system operator to better determine chronic impact of the therapy. In an embodiment, the external information receiver 226 creates recommended values of the stimulation parameters if the physiologic response is outside of a specified value range.

In another embodiment, the recommendation of stimulation parameters is performed when the system is in a temporary, commended test mode. In this mode, the test parameters (including therapy on-off patterns and a combination of therapy intensity parameter values) may be programmed by a system operator in a clinical setting, or the test parameters may be generated by the system automatically with no or minimal user intervention. The stimulator delivers the stimulation pulses according to the test stimulation parameters. During the stimulation, the feedback information collector 610 acquires the feedback information and provides the feedback information to the external information receiver 226 and presents it to the system operator from the display unit 621. If the feedback information does not meet a specified criterion, then further adjustment of parameters and testing is needed. However, if the feedback information meets the specified criterion, the present test parameters are deemed acceptable and an adjustment of parameter is recommended, and the stimulator system can be switched from its current commanded temporary test mode back to the ambulatory therapy mode.

Figure 7:
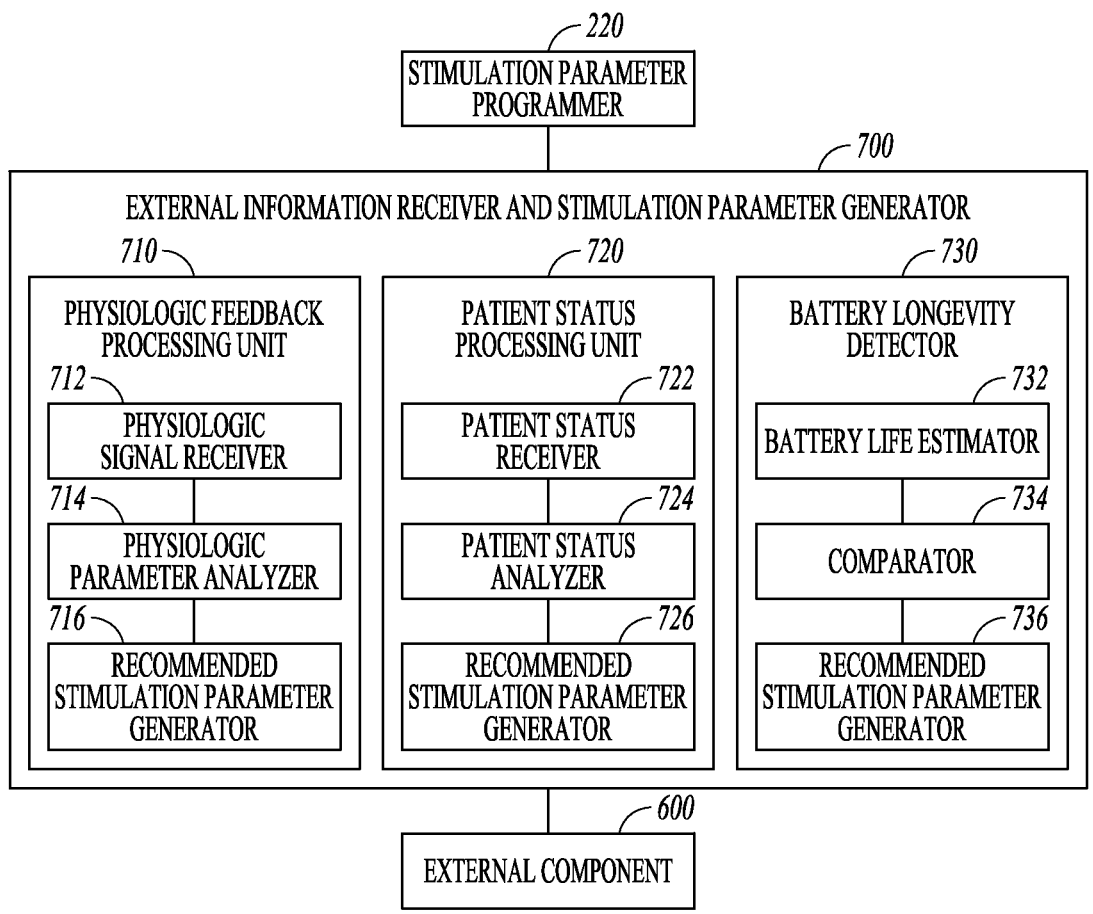
FIG. 7 illustrates, by way of example, an embodiment of a feedback receiver and therapy parameter adjuster.

FIG. 7 illustrates, by way of example, an embodiment of the feedback receiver and therapy parameter adjuster 700, which is a specific embodiment of the external information receiver 226 as shown in FIGS. 2 and 6. The external information receiver and stimulation parameter generator 700 includes a physiologic feedback processing unit 710, a patient status processing unit 720, and a battery longevity detector 730. The external information receiver and stimulation parameter generator 700 can receive feedback information from the feedback information collector 610 in the external components 600, generate recommended values for the one or more stimulation parameters using the feedback information, and pass the recommended values for the one or more stimulation parameters to the stimulation parameter programmer 220. In some embodiments, the external information receiver and stimulation parameter generator 700 can pass the recommended values for the stimulation parameters to the user interface unit 620 in the external components 600, where the recommended stimulation parameters can be presenting to the system operator.

The physiologic feedback processing unit 710 includes a physiologic signal receiver 712 configured to receive the physiologic signal acquired by physiologic sensors during the therapy delivery. In some embodiments, the physiologic signal can be provided by the feedback information collector 610. The physiologic signal can be processed by a physiologic parameter analyzer 714. The processing performed by the physiologic parameter analyzer can include amplification, filtering, and signal transformation. The physiologic parameter analyzer 714 can also extract signal features and compute a signal metric indicative of the effectiveness of the stimulation therapy. The recommended stimulation parameter generator 716 can compare the signal metric to a threshold, and provide a recommended value for one or more stimulation parameters based on that comparison.

In one embodiment, the physiologic signal receiver 712 receives an arterial blood pressure signal from a physiologic sensor in the external component 600. The physiologic parameter analyzer 714 detects systolic and diastolic pressure values from the blood pressure signal and computes a mean arterial pressure during stimulation therapy ($MAP_S$). The recommended stimulation parameter generator 716 compares the computed $MAP_S$ to a threshold MAP value. Alternatively, the recommended stimulation parameter generator 716 computes a relative change (Δ% MAP) in MAP during stimulation therapy with respect to a pre-therapy baseline MAP level ($MAP_B$), that is, $\Delta\% \text{ MAP}=(MAP_B-MAP_S)/MAP_B$, and compares Δ% MAP to a threshold of relative change in MAP. If the $MAP_S$ is above the threshold MAP, or if Δ% MAP is less than the threshold of relative change in MAP, the blood pressure is deemed inadequately reduced and the AHT stimulation therapy ineffective. The recommended stimulation parameter generator 716 may then recommend a therapy on-off pattern with a shortened or gradual decrease in therapy-off duration as illustrated in FIG. 5D, a prolonged or gradual increase in therapy-on duration as illustrated in FIG. 5A, or an increase in stimulation strength during the therapy-on periods (e.g., an increase in pulse amplitude, pulse width, frequency, or pulse duty cycle). However, if the $MAP_S$ is below the threshold MAP, or if Δ% MAP is greater than the threshold of relative change in MAP, the blood pressure is deemed adequately reduced and the AHT therapy is effective. The recommended stimulation parameter generator 716 may then recommend no change to the stimulation parameters. Alternatively, the recommended stimulation parameter generator 716 may issue a power-saving command, and recommend parameter adjustment to make the stimulation system transition from the ambulatory therapy mode to a power-saving mode. The recommended adjustment may include a prolonged or gradual increase in therapy-off duration as illustrated in FIG. 5C, a shortened or gradual decrease in therapy-on duration as illustrated in FIG. 5B, or a decrease in stimulation strength during the therapy-on periods. Such recommended stimulation parameters may reduce the system power consumption while adequately maintain therapy efficacy. In some embodiment, the power-saving command may be presented to the system operator on a user interface unit in the external component 600, where the system operator may confirm the transition into the power-saving mode by accepting the recommended value of the stimulation parameters.

The patient status processing unit 720 includes a patient status receiver 722 configured to receive patient status information before or during the therapy delivery. The patient status information can include one or more of a patient activity level, a posture, patient comfort level during therapy, and awakeness or sleep state. The patient status analyzer 724 can compute a metric and quantize it into a plurality of levels or classes. For example, in an embodiment, the patient status receiver 722 receives patient activity information from an accelerometer or a respiration sensor such as from the feedback information collector 610. The status analyzer 724 can quantize the acceleration signal or the respiration signal into one of a number of levels including, for example, "high activity", "medium activity", "low activity", and "very low activity". The recommended stimulation parameter generator 726 then recommends a parameter setting in accordance with the quantized activity level. In some embodiments, the recommended parameter setting is determined using a look-up table or an association map that associates the levels of patient status (such as the activity level) to corresponding values of one or more stimulation parameters. For example, a high activity level can be mapped a therapy on-off pattern with shortened or gradual decrease in therapy-off duration, or a prolonged or gradual increase in therapy-on duration, or an increase in stimulation strength during the therapy-on periods. Such a therapy on-off pattern can cause significant reduction in pressure, thereby preventing adverse outcome associated with elevated blood pressure during intensive activity. The therapy on-off pattern can be adjusted adaptively to achieve desirable blood pressure level during intensive activity. In another example, a low activity level (such as rest or sleep) can be mapped to a therapy on-off pattern with a prolonged or gradual increase in therapy-off duration, a shortened or gradual decrease in therapy-on duration, or a decrease in stimulation strength during the therapy-on periods. Such a therapy on-off pattern can cause mild reduction in pressure, thereby maintaining the pressure at a tolerable level during mild activity. In some embodiments, when the patient activity is below a pre-determined threshold or categorized as "low activity" or "very low activity", the recommended stimulation parameter generator 726 may issue a power-saving command, and recommend parameter adjustment according to the activity-parameter look-up table or association map to make the stimulation system transition from the ambulatory therapy mode to a power-saving mode. The power-saving command may be presented to the system operator on a user interface unit in the external component 600 for the operator's confirmation.

The battery longevity detector 730 includes a battery life estimator 732 configured to estimate the battery life at the time of therapy delivery. The battery life may be estimated using the energy stored in the battery and the present stimulation parameter setting. A comparator 734 compares the estimated battery life to a threshold to determine if the system needs to be transitioned to a power-saving mode. If the estimated battery life is above the preset threshold, then the recommended stimulation parameter generator may recommend no change to the present stimulation parameters. However, if the estimated battery life is below the preset threshold, then the recommended stimulation parameter generator 736 issues a power-saving command, recommends a stimulation parameter setting that can reduce power consumption to make the stimulation system transition from the ambulatory therapy mode to a power-saving mode. The recommended parameters may include a therapy on-off pattern with a prolonged or gradual increase in therapy-off duration, a shortened or gradual decrease in therapy-on duration, or a decrease in stimulation strength during the therapy-on periods. The power-saving command may be presented to the system operator on a user interface unit in the external component 600 for the operator's confirmation.

In various embodiments, the external information receiver and stimulation parameter generator 700 any use any combination of two or more of the physiologic feedback, patient status, battery longevity, and other external information such as those provided by the feedback information collector 610;

and recommend an adjustment of the one or more stimulation parameters. In some embodiments, the time of day (e.g., night time or day time) can be used to alter the therapy on-off pattern. For example, during the night time the system can transition from the ambulatory therapy mode to a power-saving mode; and the therapy on-off pattern under the power-saving mode can be characterized by one or more of a shortened or gradual decrease in therapy-on duration (or equivalently, more frequent therapy-off periods), a prolonged or gradual increase in therapy-off duration, or a decrease in stimulation strength during the therapy-on periods is recommended to reduce the energy consumption without causing deterioration in therapy efficacy. During the day time, the system can transition back to the ambulatory therapy mode with the original parameter setting.

Figure 8:
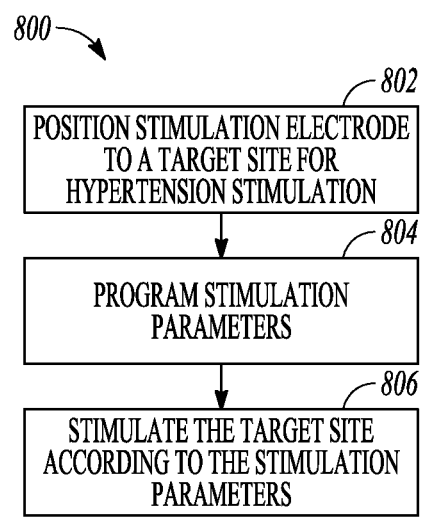
FIG. 8 illustrates, by way of example, an embodiment of a method for stimulating a target site to treat hypertension in a patient.

FIG. 8 illustrates, by way of example, an embodiment of a method 800 for stimulating a target site to treat hypertension in a patient. In an embodiment, the implantable stimulator system 100, including its various embodiments discussed in this document, is programmed to perform method 800, including its various embodiments discussed in this document. The method 800 starts at 802 with positioning one or more stimulation electrodes to a target site for an AHT therapy. Examples of the target stimulation site include various sites on an exterior of a carotid artery or other baroreceptor region, aortic arch, carotid sinuses of the left and right internal carotid arteries, carotid body, carotid sinus, cardiac fat pads, and vena cava. Additionally, a baroreceptor region can include one or more of afferent nerve trunks, such as the vagus, aortic and carotid nerves, leading from the sensory nerve endings. The electrodes can be temporarily or chronically positioned to the tissue at the target site. In an embodiment, the electrodes are temporarily positioned to the target site for acute testing. This may be performed, for example, in a clinical setting during the implant of the stimulation system. The electrodes can be configured to be temporarily positioned to a target site and be easily removed from the target site and positioned to a different target site, until a desirable site of stimulation is found. In another embodiment, the electrodes are configured to be chronically implanted to the target site for chronic and ambulatory therapy.

At 804, one or more stimulation parameters are programmed. The programmed stimulation parameters determine the waveform, strength, and the schedule of the pulse train. In some embodiments, the stimulation parameters may include parameters controlling the stimulation pulse waveform and the strength such as pulse amplitude, pulse width, inter-pulse interval, pulse duty cycle, pulse frequency, pulse waveform or morphology. Pulse waveform may include square wave, triangle wave, sinusoidal wave, and waves with desired harmonic components to mimic white noise such as is indicative of naturally-occurring baroreflex stimulation. Pulse waveform may also be in the form of multiphasic waves including biphasic, triphasic, or multiphasic waves. These parameters control the amount of energy delivered to the target site within a unit time. In an embodiment, programming the stimulation parameters can include adjusting stimulation strength by increasing or decreasing pulse width, pulse frequency, pulse amplitude, and pulse duty cycle.

In various embodiments, the stimulation parameters may also include therapy schedule parameters. The therapy schedule parameters control the time and duration of the stimulation pulse train, which may include a therapy-on period during which the stimulation pulses are programmed to be delivered, a therapy-off period during which no stimulation pulse is programmed to be delivered, and a therapy on-off pattern. The therapy on-off pattern may include the timing of the initiation of the stimulation on period and the initiation of the stimulation off period. In some embodiments, the therapy on-off pattern can include a combination of a set of therapy-on periods with variable durations and a set of therapy-off periods with variable durations. In one example, the therapy on-off pattern can include at least one of a sequence of therapy-off periods with gradually increased durations, a sequence of therapy-on periods with gradually decreased durations, a sequence of therapy-on periods with gradually increased durations, and a sequence of therapy-off periods with gradually decreased durations.

Programming of the stimulation parameters may be performed with or without system operator's intervention. In an embodiment, the stimulation parameters are programmed by a system operator (e.g., a clinician) using a user input device such as the user interface 620 as illustrated in FIG. 6. In another embodiment, the stimulation system can automatically program the one or more stimulation parameters without system operator's intervention.

At 806, the stimulation pulse train can be delivered to the target site in accordance with the programmed stimulation parameters. In some embodiments, programming of stimulation parameters 804 and the stimulation of the targets site 806 may be performed iteratively by sweeping through a set of parameter settings to determine a desirable stimulation parameter for chronic therapy. The stimulation pulses may be delivered to the stimulation electrodes to stimulate the target site via a lead connected to the simulator system. The lead may be external to the patient, or it may be subcutaneously or transvenously placed inside the patient's body. In some embodiments, the stimulation can be delivered to the electrodes via acoustic, radiofrequency, or other wireless links.

Figure 9:
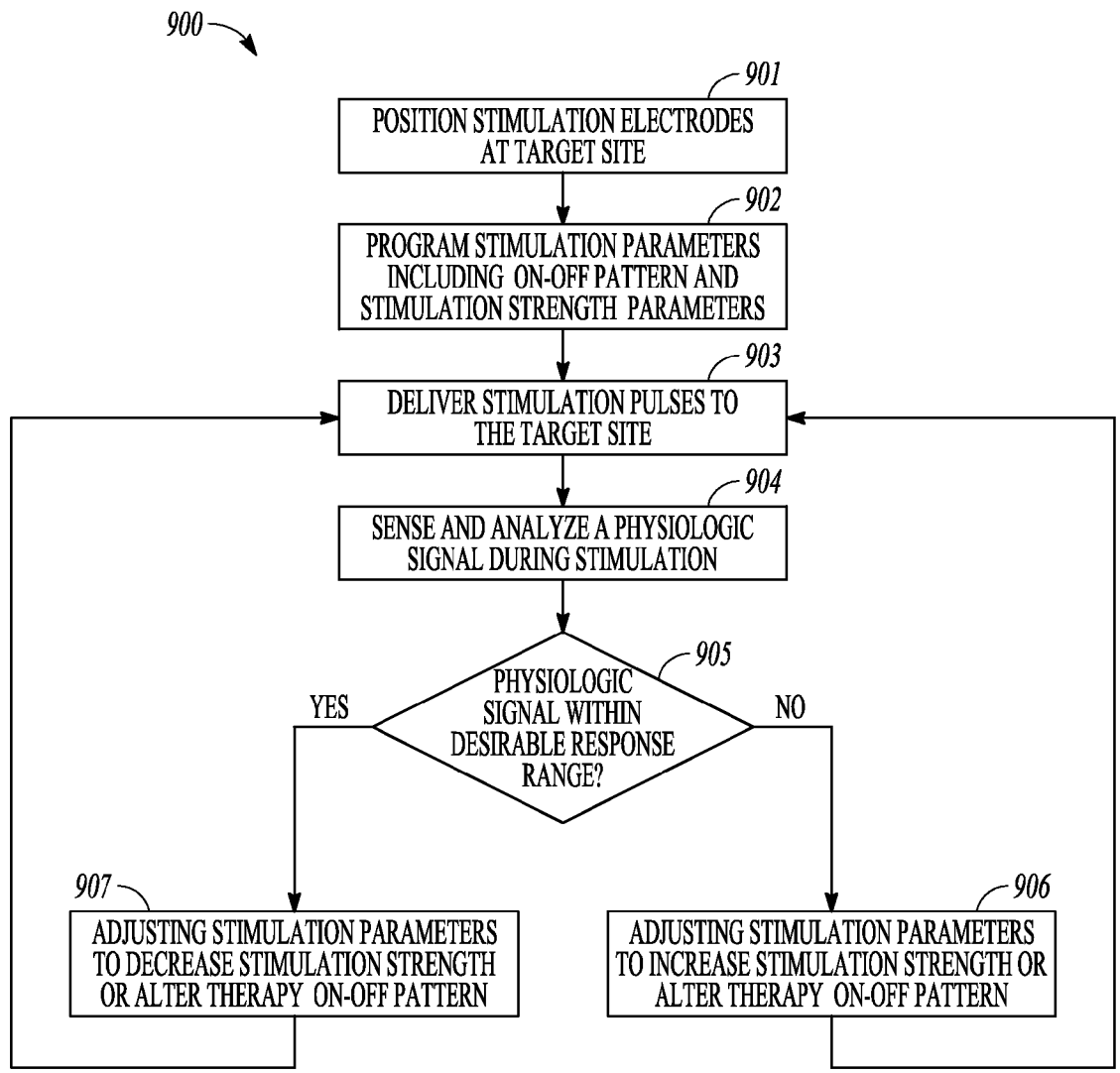
FIG. 9 illustrates, by way of example, an embodiment of a method of physiologic feedback-controlled stimulation of a target site to treat hypertension.

FIG. 9 illustrates, by way of example, an embodiment of a method 900 of physiologic feedback-controlled stimulation of a target site to treat hypertension. The method 900 represents an embodiment of method 800.

The method starts at 901 by positioning electrodes at the target site. At 902, one or more stimulation parameters, including a therapy on-off pattern and stimulation strength parameters, can be programmed. In an embodiment, the stimulation parameters can be programmed to default values expected to cause a therapeutic effect or clinically meaningful reduction in blood pressure. The default values can be determined according to the patient's AHT therapy history or population-based record of AHT treatment. In some embodiments, the stimulation parameters are initialized to high pulse amplitude, high pulse frequency, large pulse width, and a therapy on-off pattern with one or more of long therapy-on period, short therapy-off period, and less frequent therapy-off periods. At 903, the programmed stimulation pulses are delivered to the target site. During the stimulation, the physiologic signal can be sensed at 904. The physiological signal can include one or more of electrocardiogram, electrograms, arterial pressure, pulmonary artery pressure, RV pressure, LV coronary pressure, coronary blood temperature, blood oxygen saturation, heart sounds, respiration signals, nerve activity, nerve traffic, and other ANS activity. Examples of physiologic sensor may include an implantable or ambulatory sensor configured to sense the physiologic response, and an external invasive or noninvasive physiologic monitor configured to sense the physiologic response. The physiologic sensor may also include one or more modalities including impedance, acceleration, pressure, temperature, mechanical strain or stress, and other signals indicative of the changes in physiologic responses to the stimulation. The sensed physiologic signal can be processed and analyzed to determine a characteristic physiologic metric in response to the stimulation. In one example, a blood pressure signal during the stimulation can be sensed, and the change in mean arterial pressure (MAP) from the pre-stimulation MAP level can be determined.

At 905, the physiologic signal or the characteristic physiologic metric is compared to a desirable response range to determine if a pre-determined criterion is met. In some embodiments, the desirable response range may include a threshold value of the change of the MAP during stimulation from a pre-stimulation baseline MAP level. In some embodiments, the desirable response range may include a threshold value of the MAP level during stimulation. If at 905 the physiologic signal is outside the desirable response range (for example, MAP during stimulation is above a threshold level), then the stimulation therapy is deemed ineffective; and at 906 the one or more stimulation parameters can be adjusted to increase the stimulation energy delivered to the target site. In an embodiment, energy may be increased by programming increased stimulation strength with a higher pulse amplitude, longer pulse width, and higher pulse frequency. In another embodiment, the energy may be increased by choosing a therapy on-off pattern with a longer therapy-on period, a shorter therapy-off period, and less frequent therapy off-periods. In yet another embodiment, the therapy on-off pattern may be adjusted in a "step-up" or "step-down" fashion such that the therapy-off period can be gradually shortened as illustrated in FIG. 5D, or the therapy-on period can be gradually prolonged as illustrated in FIG. 5A. The stimulation pulses are then delivered at 903 in accordance with the newly adjusted stimulation parameters.

If at 905 the physiologic signal is within the desirable response range (for example, MAP during stimulation is below a first threshold level), then the stimulation therapy is deemed effective; and at 907 the stimulation parameters can be adjusted to reduce the energy consumption without substantially reducing the therapy efficacy. In an embodiment, the energy consumption may be reduced by programming reduced stimulation strength with lower pulse amplitude, shorter pulse width, and lower pulse frequency. In another embodiment, the energy consumption may be reduced by choosing a therapy on-off pattern with a shorter therapy-on period, a longer therapy-off period, and more frequent therapy off-periods. In some other embodiments, reduction of energy consumption may be achieved by a combination of reduced stimulation strength and a therapy on-off pattern. In yet another embodiment, the therapy on-off pattern may be adjusted in a "step-up" or "step-down" fashion such that the therapy-off period can be gradually prolonged as illustrated in FIG. 5C, or the therapy-on period can be gradually shortened as illustrated in FIG. 5B. The stimulation pulses can then be delivered at 903 in accordance with the newly adjusted stimulation parameters. In various embodiments, the adjustment of the stimulation parameters at 906 and 907 may be performed iteratively to search for values for the stimulation parameters that are effective in reducing the blood pressure while minimizing the energy consumption.

In some embodiments, in addition to or as an alternative to the adjustment of the stimulation parameter by comparing the sensed physiologic signal to a desired response range or threshold, the adjustment of stimulation parameters may be determined by referencing a look-up table or an association map stored in the stimulator system, where the look-up table or the association map associates the physiologic response to the one or more stimulation parameters. Adjustment of the one or more stimulation parameters may be determined by searching from the look-up table for the parameter setting that corresponds to the sensed physiologic response.

Figure 10:
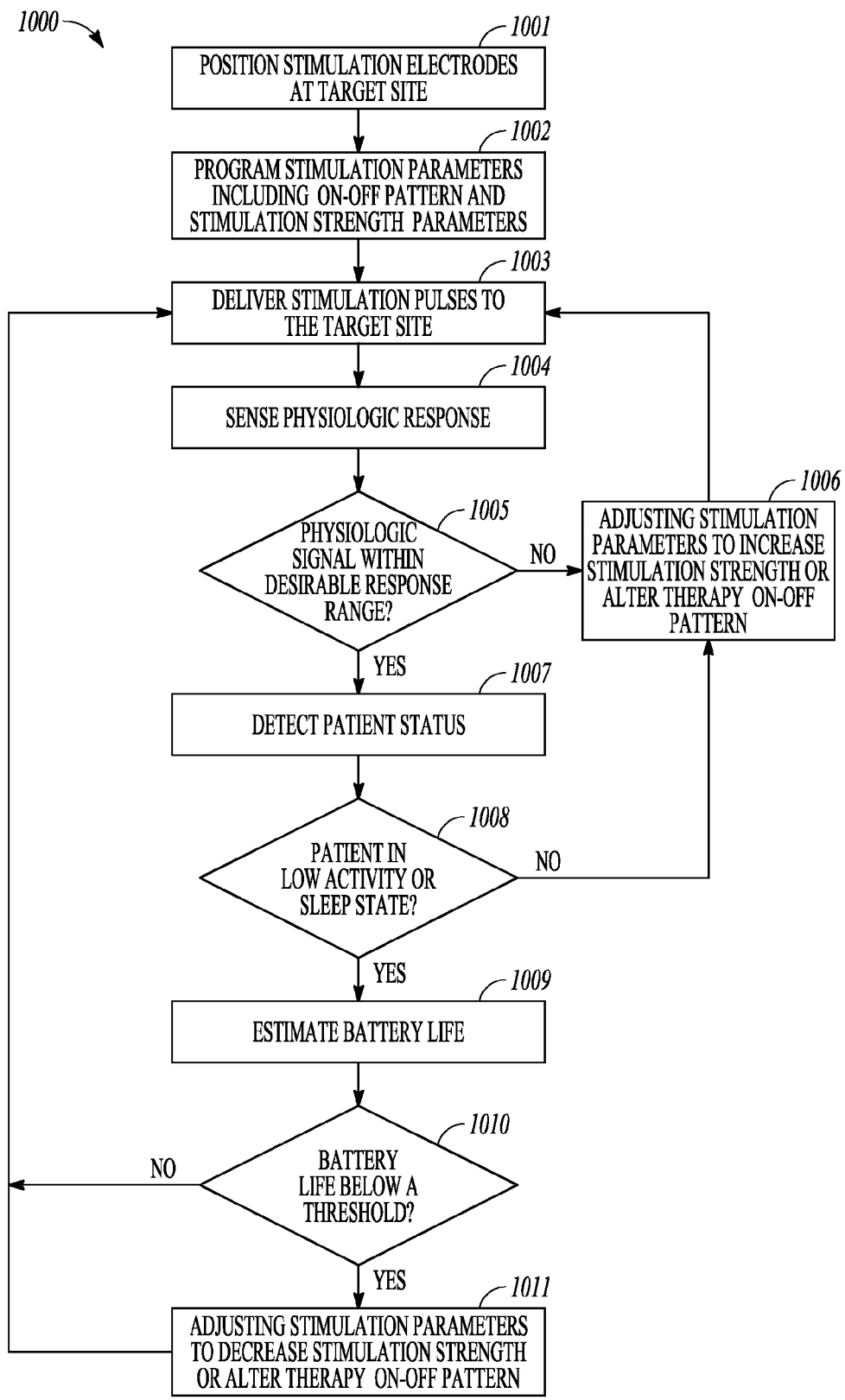
FIG. 10 illustrates, by way of example, an embodiment of a method of feedback-controlled stimulation of a target site to treat hypertension.

FIG. 10 illustrates, by way of example, an embodiment of a method 1000 of feedback-controlled stimulation of a target site to treat hypertension. The method 1000 represents another embodiment of method 800.

The method starts at 1001 by positioning electrodes at the target site. At 1002, one or more stimulation parameters are programmed, including programming a therapy on-off pattern and stimulation strength parameters. In some embodiments, the one or more stimulation parameters may be programmed to default values expected to be effective in causing a therapeutic effect or clinically meaningful reduction in blood pressure. In some embodiments, the one or more stimulation parameters are selected with strong stimulation strength and therapy on-off pattern with long therapy-on duration and short therapy-off duration. Then at 1003, the stimulation pulses are delivered to the target site in accordance with the programmed stimulation parameters. During the stimulation, the physiologic signal is sensed at 1004. In various other embodiments, the physiological signal may include electrocardiogram, electrograms, arterial pressure, pulmonary artery pressure, RV pressure, LV coronary pressure, coronary blood temperature, blood oxygen saturation, heart sounds, respiration signals, nerve activity, nerve traffic, and other ANS activity. The sensed physiologic signal can be processed and analyzed to determine a characteristic physiologic metric. At 1005, the physiologic signal or the characteristic physiologic metric is compared to a desirable response range to determine if a pre-determined criterion is met. If at 1005 the physiologic signal is outside the desirable response range, then the stimulation therapy is deemed ineffective; and at 1006 the one or more stimulation parameters may be adjusted to increase the stimulation energy delivered to the target site. In an embodiment, energy may be increased by programming increased stimulation strength with a higher pulse amplitude, longer pulse width, and higher pulse frequency. In another embodiment, the energy may be increased by choosing a therapy on-off pattern with a longer therapy-on period, a shorter therapy-off period, and less frequent therapy off-periods. In yet another embodiment, the therapy on-off pattern may be adjusted in a "step-up" or "step-down" fashion such that the therapy-off period is gradually shortened as illustrated in FIG. 5D, or the therapy-on period is gradually prolonged as illustrated in FIG. 5A. In some other embodiments, reduction of energy consumption may be achieved by a combination of reduced stimulation strength and a therapy on-off pattern. The stimulation pulses are then delivered in accordance with the newly adjusted stimulation parameters at 1003.

If at 1005 the physiologic signal is within the desirable response range (for example, MAP during stimulation is below a threshold level), then the stimulation therapy is deemed effective. Patient status, including activity level and sleep/awake state, is then detected at 1007. Patient status may be detected using a sensor internal or external to the patients. Examples of such sensors may include an accelerometer that detects the posture or activity level of the patient, a transthoracic impedance sensor that detects the minute ventilation and thereby the activity level of the patient, a bioelectric sensor detects the brain activity and thereby the sleep state or awakeness. At 1008, the patient status information is processed to determine if the patient is in low activity or in a sleep state. In an embodiment, a metric can be measured from the detected patient status signal and quantized into a plurality of levels or categorized in a plurality of classes. For example, a minute ventilation respiration signal can be quantized into one of a number of levels indicative of activity intensity, including "high activity", "medium activity", "low activity"

and "very low activity". If at 1008 the patient is found to be highly active or in awake state, a more significant reduction in blood pressure is expected to prevent the adverse outcome associated with elevated blood pressure. The therapy on-off pattern can be adjusted adaptively to achieve desirable blood pressure level during intensive activity. The method then is directed to 1006 to increase the stimulation energy delivered to the target site.

If at 1008 the patient is found to be less active or in a sleep state, then the battery life is estimated at 1009. The battery life may be estimated using the energy stored in the battery and the present stimulation parameter setting. The estimated battery life can be compared to a threshold value at 1010. If the battery life is below the threshold value, the battery life is deemed low; and at 1011 a power-saving operation can be initiated by adjusting the one or more stimulation parameters to reduce the energy consumption without substantially reducing the therapy efficacy. In an embodiment, the energy consumption may be reduced by programming reduced stimulation strength with a lower pulse amplitude, shorter pulse width, and lower pulse frequency. In another embodiment, the energy consumption may be reduced by choosing a therapy on-off pattern with a shorter therapy-on period, a longer therapy-off period, and more frequent therapy off-periods. In yet another embodiment, the therapy on-off pattern may be adjusted in a "step-up" or "step-down" fashion such that the therapy-off period is gradually prolonged as illustrated in FIG. 5C, or the therapy-on period is gradually shortened as illustrated in FIG. 5B. In some other embodiments, reduction of energy consumption may be achieved by a combination of reduced stimulation strength and a therapy on-off pattern. The stimulation pulses are then delivered in accordance with the newly adjusted stimulation parameters at 1003. If at 1010 the battery life is above the threshold value, then the power-saving operation at 1011 is bypassed and no parameter adjustment is required. The stimulation pulses can be delivered in accordance with the existing stimulation parameters at 1003.

As illustrated in FIG. 10, the power-saving operation at 1011 is activated when several conditions are satisfied, including physiologic responses being within the desirable range, patient in low activity or in sleep, and the battery life below a threshold value. Other information may also be used to activate the power-saving operation at 1011. In an embodiment, the time of day (e.g., night time or day time) can be used to alter the therapy on-off pattern. For example, during the night time, a therapy on-off pattern with shortened therapy-on periods (or equivalently, more frequent therapy-off periods) or a prolonged therapy-off periods may be recommended to reduce the energy consumption without compromising the therapy efficacy during night; while during the day time, a different therapy on-off pattern with prolonged therapy-on periods (or equivalently, less frequent therapy-off periods) or a shortened therapy-on periods may be recommended to provide more substantial reduction in blood pressure. Any combinations of two or more of these conditions can be used to activate the power-saving operation and the adjustment of the one or more stimulation parameters.

The above detailed description is intended to be illustrative, and not restrictive. Other embodiments will be apparent to those of ordinary skills in the art upon reading and understanding the above description. The scope of the invention should, therefore, be determined with references to the appended claims, along with the full scope of equivalents to which such claims are entitled.

What is claimed is:

1. A system for treating hypertension, comprising:
a stimulator configured to generate stimulation pulses;
a memory circuit configured to store one or more stimulation parameters including a therapy-on period during which the stimulation pulses are programmed to be delivered, a therapy-off period during which no stimulation pulse is programmed to be delivered, and a therapy on-off pattern including a combination of a sequence of therapy-on periods with variable durations and a sequence of therapy-off periods with variable durations; and
a controller circuit connected to the stimulator and the memory circuit, the controller circuit configured to:
receive a power-saving command;
time one or both of the therapy-on period and the therapy-off period; and
schedule the delivery of the stimulation pulses to a target site according to the therapy on-off pattern in response to a power-saving command.

2. The system of claim 1, wherein the controller circuit is configured to schedule the delivery of the stimulation pulses according to the therapy on-off pattern, the scheduling of the delivery of the stimulation pulses including scheduling a first sequence of therapy-on periods with a first duration value followed by a second sequence of therapy-on periods with a second duration value, or scheduling a third sequence of therapy-off periods with a third duration value followed by a fourth sequence of therapy-off periods with a fourth duration value.

3. The system of claim 1, wherein the controller circuit is configured to schedule the delivery of the stimulation pulses according to the therapy on-off pattern, the scheduling of the delivery of the stimulation pulses including scheduling at least one of a sequence of therapy-on periods with gradually increased durations, a sequence of therapy-on periods with gradually decreased durations, a sequence of therapy-off periods with gradually increased durations, and a sequence of therapy-off periods with gradually decreased durations.

4. The system of claim 1, wherein the controller circuit is further configured to adjust stimulation strength during the therapy-on period in response to the power-saving command, the adjustment of the stimulation strength including adjustment of at least one of a pulse width, a pulse frequency, a pulse amplitude, and a pulse duty cycle within the stimulation-on period.

5. The system of claim 1, wherein the controller circuit is configured to increase one or both of the duration of the stimulation-off period and an occurrence frequency of the stimulation-off period, or to reduce the stimulation strength during the stimulation-on period.

6. The system of claim 1, further comprising a physiologic response detector configured to detect a physiologic signal during the stimulation, wherein the controller is configured to generate or receive from a system operator a power-saving command using the physiologic signal.

7. The system of claim 6, wherein:
the physiologic response detector is configured to sense a blood pressure signal and detect a blood pressure metric; and
the controller is configured to generate or receive from the system operator the power-saving command in response to the blood pressure metric falling below a blood pressure threshold.

8. The system of claim 1, further comprising a patient status detector configured to detect a patient status during the stimulation, the patient status including one or more of a patient comfort level during stimulation, a posture, an activity level, and a patient disease state, wherein the controller is configured to generate or receive from a system operator the power-saving command using the patient status.

9. The system of claim 8, wherein:
the patient status detector is configured to detect an activity signal indicating the patient's activity level; and
the controller is configured to generate or receive from the system operator the power-saving command in response to the patient's activity level falling below an activity threshold.

10. The system of claim 1, further comprising a battery configured to power up the stimulator and a battery longevity detector configured to estimate a remaining life of the battery, wherein the controller is configured to generate or receive from the system operator the power-saving command in response to the estimated remaining battery life falling below a battery life threshold.

11. The system of claim 1, further comprising a user interface and a user input device, wherein:
the user interface is configured to present at least one of a patient condition and a system condition, the patient condition including at least one of the physiologic signal during the stimulation and the patient status, the system condition including at least one of the therapy on-off pattern, the stimulation strength, and the estimated battery life; and
the user input device is coupled to the controller circuit and is configured to receive input from the system operator, the received input including one or more stimulation parameters.

12. A method for treating hypertension, comprising:
receiving a power-saving command;
programming one or more stimulation parameters in response to the power-saving command, the one or more stimulation parameters including a therapy-on period during which stimulation pulses are programmed to be delivered, a therapy-off period during which no stimulation pulse is programmed to be delivered, and a therapy on-off pattern defining a combination of a sequence of therapy-on periods with variable durations and a sequence of therapy-off periods with variable durations;
generating the stimulation pulses in accordance with the one or more stimulation parameters; and
delivering the stimulation pulses to a target site.

13. The method of claim 12, wherein delivering the stimulation pulses to the target site includes delivering the stimulation pulses to at least one of a baroreceptor region and a vagus nerve region subcutaneously or transvenously.

14. The method of claim 12, wherein programming the one or more stimulation parameters includes programming a first sequence of therapy-on periods with a first duration value followed by a second sequence of therapy-on periods with a second duration value, or a third sequence of therapy-off periods with a third duration value and a fourth sequence of therapy-off periods with a fourth duration value.

15. The method of claim 12, wherein programming the one or more stimulation parameters includes programming at least one of a sequence of therapy-on periods with gradually increased durations, a sequence of therapy-on periods with gradually decreased durations, a sequence of therapy-off periods with gradually increased durations, and a sequence of therapy-off periods with gradually decreased durations.

16. The method of claim 12, wherein programming the one or more stimulation parameters includes programming one or more stimulation strength parameters including a pulse width, a pulse frequency, a pulse amplitude, and a pulse duty cycle within the stimulation-on period.

17. The method of claim 12, further comprising detecting a physiologic signal during the delivery of the stimulation pulses, wherein:
receiving the power-saving command includes generating or receiving from a system operator the power-saving command in response to the physiologic signal indicating a desirable reduction in blood pressure; and
programming the one or more stimulation parameters includes one or more of increasing the duration of the stimulation-off period, increasing an occurrence frequency of the stimulation-off period, and reducing the stimulation strength during the stimulation-on period, in response to the power-saving command.

18. The method of claim 17, wherein detecting the physiologic signal includes sensing a blood pressure signal and detecting a blood pressure metric from the blood pressure signal; and
receiving the power-saving command includes generating or receiving from the system operator the power-saving command in response to the blood pressure metric falling below a blood pressure threshold.

19. The method of claim 12, further comprising detecting a patient status during the delivery of the stimulation pulses, the patient status including one or more of a patient comfort level during stimulation, a posture, an activity level, and a patient disease state, and wherein:
receiving the power-saving command includes generating or receiving from the system operator the power-saving command in response to the patient status meeting a specified criterion; and
programming the one or more stimulation parameters includes one or more of increasing the duration of the stimulation-off period, increasing an occurrence frequency of the stimulation-off period, and reducing the stimulation strength during the stimulation-on period, in response to the power-saving command.

20. The method claim 12, further comprising estimating a remaining life of a battery used for generating stimulation pulses, wherein:
receiving the power-saving command includes generating or receiving from the system operator the power-saving command in response to the estimated remaining battery life falling below a battery life threshold; and
programming the one or more stimulation parameters includes one or more of increasing the duration of the stimulation-off period, increasing an occurrence frequency of the stimulation-off period, and reducing the stimulation strength during the stimulation-on period, in response to the power-saving command.

* * * * *